United States Patent [19]
Leist et al.

[11] 4,334,541
[45] Jun. 15, 1982

[54] THERMAL PROTECTIVE CIRCUIT FOR A HYPEREMIA-INDUCING PHYSIOLOGICAL SENSOR

[75] Inventors: Helmut Leist; Georg J. Ullrich, both of Freiburg im Breisgau, Fed. Rep. of Germany

[73] Assignee: Hellige, GmbH, Freiburg im Breisgau, Fed. Rep. of Germany

[21] Appl. No.: 130,639

[22] Filed: Mar. 17, 1980

[30] Foreign Application Priority Data

Mar. 24, 1979 [DE] Fed. Rep. of Germany ....... 2911601

[51] Int. Cl.³ .............................................. A61B 5/00
[52] U.S. Cl. .................................... 128/632; 128/635
[58] Field of Search ............................. 128/631–635, 128/736, 742, 399, 401; 337/1, 14, 385, 298

[56] References Cited

U.S. PATENT DOCUMENTS

| | | | |
|---|---|---|---|
| 1,749,718 | 3/1930 | Randolph et al. | 337/385 |
| 3,516,411 | 6/1970 | Adler | 128/399 |
| 4,005,700 | 2/1977 | Parker | 128/632 |
| 4,186,294 | 1/1980 | Bender | 128/399 |
| 4,190,053 | 2/1980 | Sterzer | 128/399 X |
| 4,252,123 | 2/1981 | Kimmich | 128/635 |

*Primary Examiner*—Henry J. Recla
*Assistant Examiner*—Francis T. Jaworski
*Attorney, Agent, or Firm*—Richard Zentner; Walter R. Thiel

[57] ABSTRACT

A sensor for transcutaneous measurement of physiological phenomena of living tissues is provided with a thermostatically-controlled electric heater. The purpose of the heater is to induce local hyperemia to enable operation of the sensor. The heater is thermostatically controlled. An independent temperature sensor is provided to disable the heater in the event of catastrophic failure of the thermostat circuit.

4 Claims, 5 Drawing Figures

4,334,541

THERMAL PROTECTIVE CIRCUIT FOR A HYPEREMIA-INDUCING PHYSIOLOGICAL SENSOR

BACKGROUND OF THE INVENTION

1. Technical Field of the Invention

This invention is concerned with a fail-safe thermal protective circuit for a heater element employed in a hyperemia-inducing physiological sensor.

2. Description of the Prior Art

For medical diagnostic purposes, various types of physiological sensors may be employed. Such sensors are used for transcutaneous measurement and monitoring of various physiological phenomena, without puncturing the skin of the patient. Typical applications are measurements of blood flow, blood oxygen content, sugar content, alcohol content, carbon dioxide content, blood pH, etc. Typically, such devices are attached to the patient externally. The sensor is heated by an internal heating element for the purpose of local hyperemization at the site of the sensor.

Usually the internal heating element is electrical, although fluid-heated elements are known. Ordinarily the desired temperature range is on the order of 37 to 45 degrees C. (98.6 degrees to 113 degrees F.) and is controlled by a suitable thermostat. It is preferable that the sensor itself be constrained to minimal dimensions. Accordingly, only the sensor elements, the heater and a heat sensor such as a small thermistor are mounted in the physiological sensor. The heater controls such as a thermostat, temperature indicator and heater power supply are mounted in a separate remote control module. The control module is connected to the physiological sensor by a small, multiconductor cable.

With any electrical control device, there is always the danger of a control circuit malfunction. Thus, if the thermostat itself were to malfunction, or if the temperature sensing lines from the thermistor failed, the patient would be endangered if the physiological sensor overheated.

It is known to add a second, backup temperature sensor and thermostat to take over in the event that the primary temperature-control circuit fails. However such an arrangement requires additional conductors as well as additional complexity in the remote control module.

Accordingly, it is an object of this invention to provide a thermal protective circuit that is built into the sensor itself, that will automatically cut off the heating element in the sensor independently of the heater-control system in the event of a catastrophic failure of the conventional thermostatic temperature-control circuitry.

SUMMARY OF THE INVENTION

In accordance with a preferred aspect of this invention, a physiological sensor is heated by a thermostatically controlled, internal heater which may be electrically powered. An independent over-temperature thermal protective circuit is mounted internally of the physiological sensor for interrupting the power to the heater when the temperature thereof exceeds a predetermined level.

In another aspect of this invention a remote control module including a heater power supply is provided. The remote control module is coupled to the physiological sensor by a multiconductor cable including a pair of power leads for interconnecting the power supply with the heater. A normally-closed over-temperature switch cooperating with a latching relay, mounted adjacent the heater, is coupled in series with one of the power leads. The switch opens to irreversibly interrupt the heater power upon sensing an excessive temperature rise.

In another aspect of this invention, the over-temperature switch is a fusible link in series with one of the power leads. When the temperature exceeds a predetermined level, the fusible link melts, irreversibly cutting off the power to the heater.

In another aspect of this invention, a normally open over-temperature switch is connected in shunt across the heater. Upon sensing an excessive temperature rise, the switch closes to short-circuit and disable the heater. The current increase due to the short circuit trips a breaker in the control module to disconnect heater power.

DETAILED DESCRIPTION OF THE PREFERRED EMBODIMENT

Figure 1:
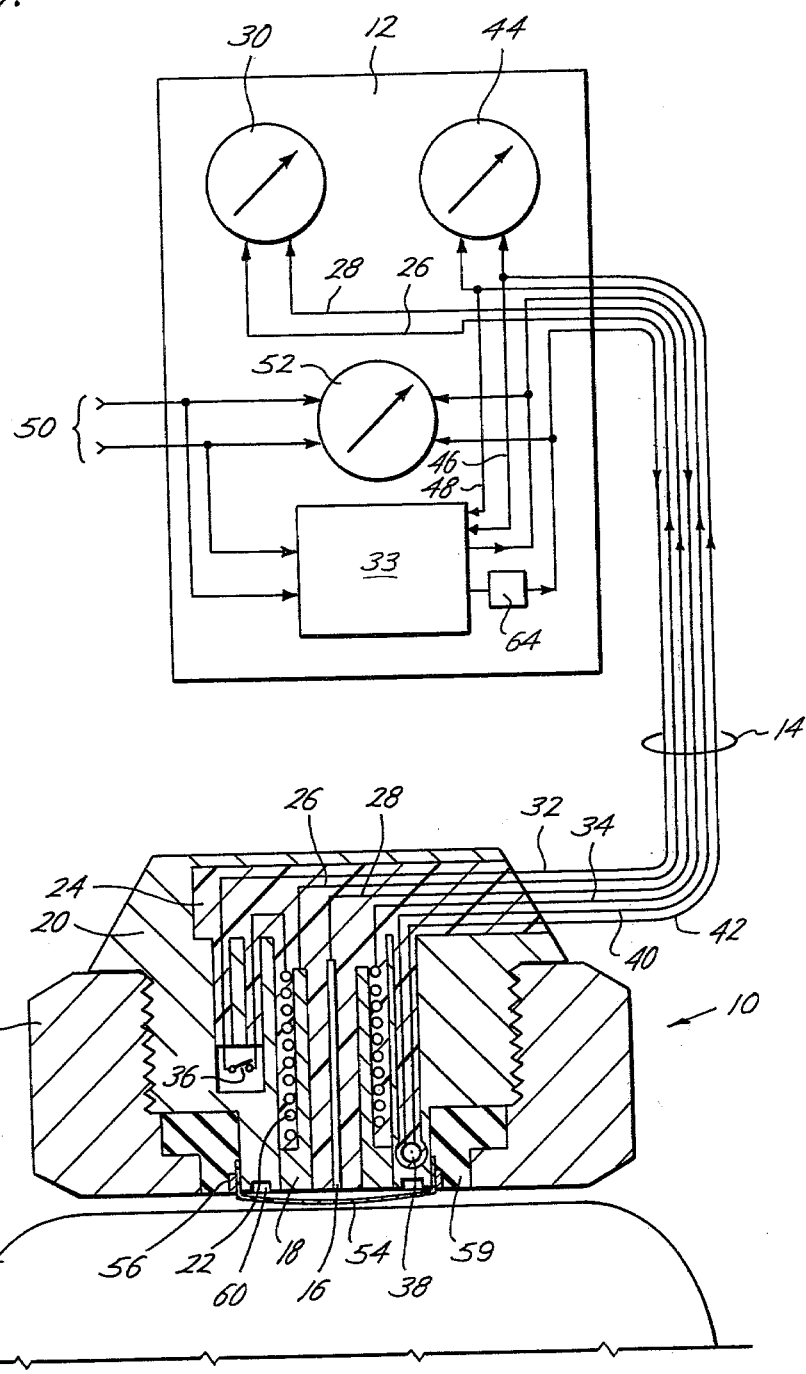
FIG. 1 is a cross-sectional view of a physiological sensor employing the over-temperature protective circuit of this invention.

Referring now to FIG. 1, there is shown a physiological sensor 10, coupled to a remote control unit 12 by means of a multiconductor cable 14 for sending power and control signals to and for receiving measurement signals from the sensor. By way of example, but not by way of limitation, physiological sensor 10 may be a polarimeter for transcutaneous determination of the concentration of gases such as oxygen, in the blood of a patient. Typical sensors are of the Clark type and are usually in the form of a circular plate a few centimeters in diameter. The sensor is then placed in direct contact with the skin 11 of a patient.

In the sensor of FIG. 1, a cathode 16, preferably platinum, and a reference electrode 18 are mounted inside an enclosure 20. A heater coil 22 surrounds reference electrode 18. A chamber 24, inside enclosure 20, is filled with a suitable electrically-insulating potting compound to insulate cathode 16, reference electrode 18, and heater coil 22 from one another and from enclosure 20. Conductors 26, 28 in cable 14 transmit the polarometric current, flowing between cathode 16 and reference electrode 18, to a suitable recording or indicating instrument 30 mounted on remote control module 12. Conductors 32, 34 in cable 14 provide power from heater power supply 33 in control unit 12 to heater coil 22 via a thermal protective circuit 36 to be described below in connection with FIG. 2. A temperature sensor 38, such as a thermistor, is mounted in physiological sensor 10 to provide signals over conductors 40, 42 in cable 14 to an indicator 44 in control unit 12 for monitoring the temperature of sensor 10. Signals from temperature sensor 38 are also transmitted to heater power supply 33 over leads 46, 48 to provide thermostatic control of heater power to heater 22. External power is applied to the system through plug 50 and power fluctuations are monitored by a suitable meter 52.

A thin membrane 54 covers the lower faces of cathode 16 and reference electrode 18. Membrane 54 is held in place and is sealed by a retaining ring 56 which in turn is secured by threaded ring 58 and sealing gasket 59 to enclosure 20. A suitable electrolyte is contained in the space 60 between membrane 54 and electrode 16 and 18. Membrane 54 may be of plastic such as polyethylene, polypropylene or polytetraflourethylene. The essential qualities of membrane 54 are that it be permeable to the diffused gases to be measured but impermeable to the electrolyte.

Normally, the temperature of physiological sensor 10 is maintained constant by means of a conventional thermostat circuit in power supply 33, under control of temperature sensor 38. In event of a malfunction of the thermostat circuit, thermal protective circuit 36 disables the heater circuit until the malfunction has been corrected.

Figure 2:
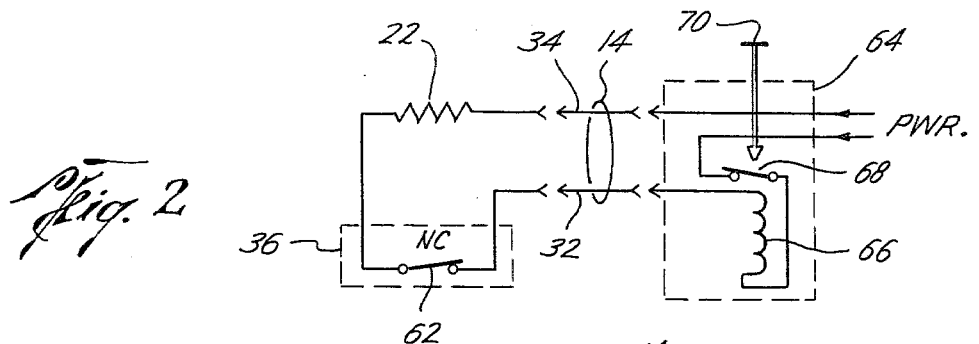
FIG. 2 is a schematic diagram of one embodiment of an over-temperature protective circuit, employing a normally closed series switch with a latching relay.
Figure 3:
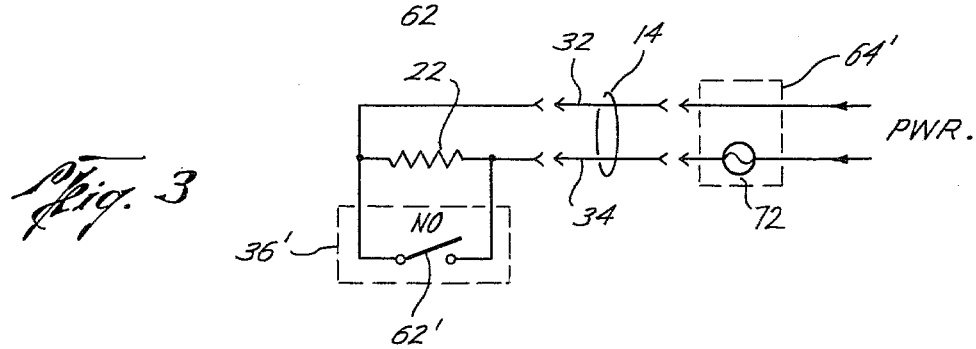
FIG. 3 is a schematic diagram of an over-temperature protective circuit employing a normally-open shunt switch in combination with a circuit breaker.
Figure 4:
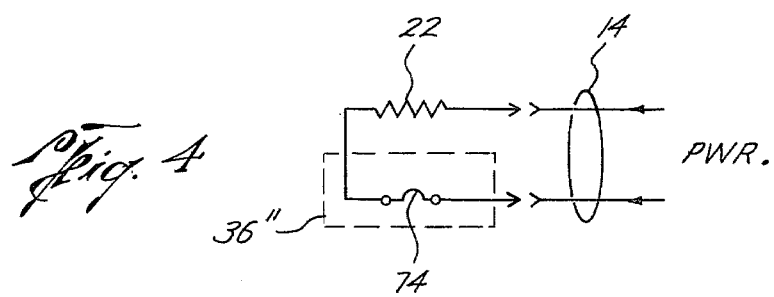
FIG. 4 is a schematic diagram of an over-temperature protective circuit employing a fusable link in series with the heater power circuit.

The thermal protective circuit represented generally by 36 of FIG. 1 is shown in greater detail in FIG. 2 with alternate arrangements being shown in FIGS. 3 and 4. In the embodiment of FIG. 2, the thermal protective circuit consists of a normally-closed temperature-sensitive switch 62 connected in series with heater 22, shown schematically as a resistor. If the temperature of sensor 10 exceeds a predetermined level, switch 62 opens to cut off the power to heater 22. Switch 62 may be of any type of temperature-sensitive configuration such as a bimetallic mechanical switch, a semiconductor switch having a suitable temperature coefficient, a mercury-silver contact thermometer or a magnetic switch employing the Curie effect using, as a magnetic latch, a ferromagnetic material such as 400 Monel which may have a Curie point as low as 43 degrees C. Also, a solid-state Hall-effect device used in combination with the above ferromagnetic material would be practical.

A simple thermal switch, as above described, used by itself is not necessarily fully protective. When sensor 10 cools after power is disconnected, switch 62 will again close. Unless the malfunction has been cleared in the meantime, overheating will again occur. Accordingly switch 62 cooperates with fail-safe circuit 64 that is mounted on remote control unit 12. Fail-safe circuit 64 includes a manually actuated latching relay having a normally-open contact arm 68. A manual reset button 70 is provided. Under ordinary conditions, switch 62 is normally closed. To turn on heater 22, reset button 70 is pressed to close contact arm 68, thereby applying power to heater 22. The current drawn by heater 22 holds latching relay 66 closed as shown. If now, switch 62 opens due to overheating, relay 66 necessarily releases contact 68 due to lack of a holding current. Under that condition, if switch 62 again closes, the heater will remain irreversibly inoperative absent operator intervention.

In another embodiment, as shown in FIG. 3, the thermal protective circuit 36' includes a normally-open switch 62' that is connected in shunt across heater 22. Upon sensing an over-temperature, switch 62' closes, short-circuiting heater 22. Of course, since a short-circuit of the power leads would destructively overheat leads 32, 34, fail-safe circuit 64' includes a protective over-current breaker of conventional style or a conventional fuse 72. The protective circuit of FIG. 3 also requires operator intervention before heater 22 can be reactivated.

Referring now to FIG. 4, thermal protective circuit 36 may consist simply of a meltable link 74 consisting of a low melting-point alloy. A preferred alloy contains 40.95% Bi, 22.10% Pb, 18.10% In, 10.65% Sr and 8.20% Cd. This alloy, which melts at 46.5 degrees C. (115.7 degrees F.) is a known quinternary eutectic alloy. Such a link provides for irreversible power interruption since power cannot be reapplied until the malfunction is cleared and a new link has been inserted.

Of the three protective-circuit options disclosed, the use of a low melting point alloy is preferred because no external circuitry is needed such as fail-safe circuits 64 or 64'. However, once the link has melted, the sensor cannot be used again until the link is replaced.

So far, the exemplary embodiment has been described in terms of an electrical heating means. It is of course, quite feasible to circulate a heated liquid through sensor 10. For such use, of course, the thermal protective devices would include thermally operated shutoff valves in conjunction with a thermally-actuated means for cutting off the fluid-circulating device.

Figure 5:
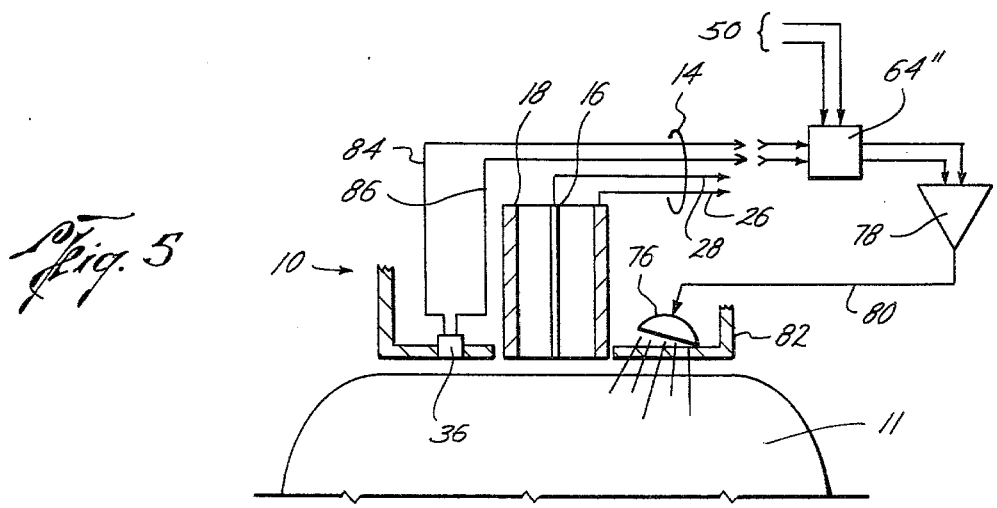
FIG. 5 illustrates schematically a physiological sensor employing diathermal heating.

In another embodiment, hyperemization may be induced by a diathermal radiator employing microwaves. Referring to FIG. 5, there is shown in schematic form, the essential elements of physiological sensor 10. For simplicity, nonessential details are not shown. A microwave radiator 76 is enclosed within physiological sensor 10 in protective enclosure 78 adjacent cathode 16 and reference electrode 18. Radiator 76 may be tilted to irradiate the patient's tissues 11 that lie beneath sensor 10. Power lines 50 provide power to a microwave generator 78 after being routed through fail-safe circuit 64". Microwave power is transmitted to radiator 76 over a suitable wave guide 80 such as coaxial cable. The thermal protective circuit is mounted inside protective enclosure 82 so that it is in direct contact with the skin of the patient. Leads 84, 86 interconnect thermal protective circuit 36 with fail-safe circuit 64". The protective action rendered by thermal protective circuit 36 may be implemented by any one of the means shown in FIGS. 2–4 wherein microwave generator 78 is substituted for heater 22. In the embodiment of FIG. 5, the microwave radiation heats the tissues but not the physiological sensor itself. Accordingly the heat generated in the tissues passes by convection through the tissues directly to thermal protective circuit 36 which is in direct contact with the skin. Thus, in FIG 5, the action of thermal protective circuit is controlled by skin temperature rather than by the temperature of a sensor heater.

We claim as our invention:

1. A physiological sensor for the transcutaneous determination of physiological phenomena, comprising a heater element;

a remote source of power for energizing the heater element;

control means, including the power source, the heater element and a first temperature-responsive device, for thermostatically maintaining the temperature of the sensor substantially constant during normal use of the sensor; and safety means, including a second temperature-responsive device, for interrupting energization of the heater element by maintaining the heater element disconnected from the power source whenever, due to failure of the control means, the temperature of the sensor exceeds a predetermined ceiling level, until intervention by an operator restores energization conditions.

2. Sensor in accordance with claim 2, wherein the safety means include a normally-closed temperature-sensitive switch cooperating with a latching relay which is resettable by hand.

3. Sensor in accordance with claim 2, wherein the safety means include an alloy link of the nature of a fuse.

4. Sensor in accordance with claim 3, wherein the melting point of the alloy link is 46.5° Centigrade.

* * * * *